(12) United States Patent
Richter et al.

(10) Patent No.: US 11,458,284 B2
(45) Date of Patent: Oct. 4, 2022

(54) CATHETER TIP ASSEMBLED WITH A SPRING

(71) Applicant: Medinol Ltd., Tel Aviv (IL)

(72) Inventors: Jacob Richter, Arsuf (IL); Shlomit Chappel, Ramat Hasharon (IL)

(73) Assignee: Medinol Ltd., Tel Aviv (IL)

( * ) Notice: Subject to any disclaimer, the term of this patent is extended or adjusted under 35 U.S.C. 154(b) by 250 days.

(21) Appl. No.: 16/545,036

(22) Filed: Aug. 20, 2019

(65) Prior Publication Data

US 2019/0366037 A1    Dec. 5, 2019

Related U.S. Application Data

(63) Continuation of application No. 15/703,162, filed on Sep. 13, 2017, now Pat. No. 10,426,923, which is a continuation of application No. 14/170,925, filed on Feb. 3, 2014, now Pat. No. 9,789,283.

(51) Int. Cl.
   *A61M 25/00*     (2006.01)
   *A61F 2/958*     (2013.01)

(52) U.S. Cl.
   CPC .......... *A61M 25/008* (2013.01); *A61F 2/958* (2013.01); *A61M 2025/0081* (2013.01)

(58) Field of Classification Search
   CPC ......... A61M 25/008; A61M 2025/0081; A61F 2/958
   See application file for complete search history.

(56) References Cited

U.S. PATENT DOCUMENTS

| | | |
|---|---|---|
| 1,899,914 A | 2/1933 | Pflueger |
| 3,618,613 A | 11/1971 | Schulte |
| 3,981,297 A | 9/1976 | Dunn et al. |
| 4,044,765 A | 8/1977 | Kline |

(Continued)

FOREIGN PATENT DOCUMENTS

| | | |
|---|---|---|
| CA | 2703926 | 5/2014 |
| CN | 101001658 | 7/2007 |

(Continued)

OTHER PUBLICATIONS

International Search Report and Written Opinion from related PCT Application No. PCT/IB2011/000401 dated Jul. 6, 2011, 16 pages.

(Continued)

*Primary Examiner* — Amber R Stiles
(74) *Attorney, Agent, or Firm* — Cadwalader, Wickersham & Taft LLP (57) ABSTRACT

A catheter tip having a spring element that imparts longitudinal flexibility, pushability and radial rigidity to the catheter tip, thereby improving deliverability, is provided. The spring element also provides radial support to the distal edge of the catheter tip. The spring element may taper distally, but may have a substantially constant inner luminal diameter. The spring element may be partially covered or embedded, leaving its distal end exposed. The spring element may also include spaced coils in a proximal region. The apparatus may be used with any interventional catheter system, but is particularly suitable for use with balloon-expandable stent systems and balloon-angioplasty systems, where flexibility of the catheter tip and minimal flaring of the distal edge of the catheter tip is desirable.

38 Claims, 6 Drawing Sheets

(56) References Cited

U.S. PATENT DOCUMENTS

| | | |
|---|---|---|
| 4,215,703 A | 8/1980 | Willson |
| 4,616,652 A | 10/1986 | Simpson |
| 4,665,604 A | 5/1987 | Dubowik |
| 4,705,511 A | 11/1987 | Kocak |
| 4,734,093 A | 3/1988 | Bonello et al. |
| 4,793,350 A | 12/1988 | Mar et al. |
| 4,838,268 A | 6/1989 | Keith et al. |
| 4,846,174 A | 7/1989 | Willard et al. |
| 4,927,413 A | 5/1990 | Hess |
| 4,985,022 A | 1/1991 | Feamot et al. |
| 5,112,304 A | 5/1992 | Barlow et al. |
| 5,195,954 A | 3/1993 | Schnepp-Pesch |
| 5,234,451 A | 8/1993 | Osypka |
| 5,243,997 A | 9/1993 | Uflacker et al. |
| 5,256,145 A | 10/1993 | Atkinson et al. |
| 5,279,596 A | 1/1994 | Castaneda et al. |
| 5,308,324 A | 5/1994 | Hammerslag et al. |
| 5,344,395 A | 9/1994 | Whalen et al. |
| 5,378,234 A | 1/1995 | Hammerslag et al. |
| 5,387,225 A | 2/1995 | Euteneuer et al. |
| 5,397,305 A | 3/1995 | Kawula et al. |
| 5,409,470 A | 4/1995 | McIntyre et al. |
| 5,423,755 A | 6/1995 | Kesten et al. |
| 5,458,585 A | 10/1995 | Salmon et al. |
| 5,549,580 A * | 8/1996 | Diaz .............. A61M 25/008 600/585 |
| 5,569,197 A | 10/1996 | Helmus et al. |
| 5,571,073 A | 11/1996 | Castillo |
| 5,573,520 A | 11/1996 | Schwartz et al. |
| 5,607,407 A | 3/1997 | Tolkoff et al. |
| 5,626,593 A | 5/1997 | Imran |
| 5,695,506 A | 12/1997 | Pike et al. |
| 5,833,631 A | 11/1998 | Nguyen |
| 5,865,767 A | 2/1999 | Frechette et al. |
| 5,972,019 A | 10/1999 | Engelson et al. |
| 5,989,208 A | 11/1999 | Nita |
| 6,069,965 A | 5/2000 | Takewa et al. |
| 6,391,018 B1 * | 5/2002 | Tanaka ............. A61M 25/0041 604/524 |
| 6,398,791 B1 | 6/2002 | Que et al. |
| 6,440,120 B1 | 8/2002 | Maahs |
| 6,500,147 B2 | 12/2002 | Omaleki et al. |
| 6,589,253 B1 | 7/2003 | Cornish et al. |
| 8,034,045 B1 | 10/2011 | Lyons |
| 9,789,283 B2 | 10/2017 | Richter et al. |
| 10,426,923 B2 | 10/2019 | Richter et al. |
| 2001/0007938 A1 | 7/2001 | Long |
| 2002/0010420 A1 | 1/2002 | Bagaoisan et al. |
| 2002/0065475 A1 | 5/2002 | Meguro et al. |
| 2002/0072730 A1 | 6/2002 | McGill et al. |
| 2003/0018318 A1 | 1/2003 | Melsky |
| 2003/0028153 A1 | 2/2003 | Brennan et al. |
| 2003/0191434 A1 | 10/2003 | Dorros et al. |
| 2003/0195490 A1 * | 10/2003 | Boatman ................ A61L 29/06 604/525 |
| 2003/0225434 A1 * | 12/2003 | Glantz ................ A61M 25/104 606/194 |
| 2004/0030375 A1 | 2/2004 | Pierce |
| 2004/0082879 A1 * | 4/2004 | Klint ...................... A61F 2/95 600/585 |
| 2005/0027309 A1 * | 2/2005 | Shiber .................. A61M 25/09 606/159 |
| 2005/0119606 A1 | 6/2005 | Nita |
| 2005/0154443 A1 | 7/2005 | Linder et al. |
| 2005/0245894 A1 * | 11/2005 | Zadno-Azizi ... A61M 25/10182 604/509 |
| 2006/0030835 A1 * | 2/2006 | Sherman .......... A61M 25/0012 604/526 |
| 2006/0100602 A1 | 5/2006 | Klint |
| 2006/0178653 A1 * | 8/2006 | Shimogami ....... A61M 25/0043 604/526 |
| 2007/0135830 A1 | 6/2007 | Schaeffer |
| 2007/0240817 A1 | 10/2007 | Strong et al. |
| 2007/0260224 A1 | 11/2007 | Von Oepen et al. |
| 2008/0108974 A1 | 5/2008 | Yee Roth |
| 2009/0082723 A1 | 3/2009 | Krogh et al. |
| 2009/0125043 A1 | 5/2009 | Dehnad |
| 2009/0014977 A1 | 6/2009 | Rooney et al. |
| 2009/0264910 A1 | 10/2009 | Laufer |
| 2009/0292296 A1 | 11/2009 | Pansky et al. |
| 2010/0049167 A1 | 2/2010 | Myers |
| 2011/0196315 A1 * | 8/2011 | Chappel ............ A61M 25/0069 604/264 |
| 2011/0196384 A1 | 8/2011 | Pansky |
| 2011/0245775 A1 | 10/2011 | Tekulve |
| 2011/0288532 A1 | 11/2011 | Faherty et al. |
| 2012/0130300 A1 | 5/2012 | Stavchansky et al. |
| 2012/0165789 A1 | 6/2012 | Deckard et al. |
| 2012/0165850 A1 | 6/2012 | Deckard et al. |
| 2012/0323145 A1 | 12/2012 | Nagano et al. |

FOREIGN PATENT DOCUMENTS

| | | |
|---|---|---|
| CN | 101926667 | 12/2010 |
| CN | 102205165 | 10/2011 |
| DE | 4036570 | 5/1992 |
| EA | 005391 | 2/2005 |
| EP | 0443256 | 8/1991 |
| EP | 1339355 | 9/2003 |
| JP | 63-238873 | 10/1988 |
| JP | H01-117357 | 8/1989 |
| JP | H01-198564 | 8/1989 |
| JP | H05-261114 | 10/1993 |
| JP | H06-23053 | 2/1994 |
| JP | H07-236695 | 9/1995 |
| JP | H08-501945 | 3/1996 |
| JP | 2682831 | 8/1997 |
| JP | 2000-502264 | 2/2000 |
| JP | 2001-129002 | 5/2001 |
| JP | 2001-157712 | 6/2001 |
| JP | 2001-204825 | 7/2001 |
| JP | 2002-224221 | 8/2002 |
| JP | 2003-520651 | 7/2003 |
| JP | 2003-521279 | 7/2003 |
| JP | 2005-511108 | 4/2005 |
| JP | 3638304 | 4/2005 |
| JP | 2010-022566 | 2/2010 |
| JP | 2010-513034 | 4/2010 |
| JP | 2011-078525 | 4/2011 |
| JP | 2011-512956 | 4/2011 |
| JP | 2013-518691 | 5/2013 |
| JP | 2013-518693 | 5/2013 |
| RU | 98112572 | 5/2000 |
| RU | 2207823 | 7/2003 |
| RU | 2302267 | 7/2007 |
| RU | 91674 | 2/2010 |
| SU | 1528505 | 12/1989 |
| WO | WO 93/11711 | 6/1993 |
| WO | WO 96/08196 A1 | 3/1996 |
| WO | WO 97/19644 | 6/1997 |
| WO | WO 01/08737 | 2/2001 |
| WO | WO 01/51114 | 7/2001 |
| WO | WO 2006/042157 | 4/2006 |
| WO | WO 2006/093274 | 9/2006 |
| WO | WO 2008/019696 | 2/2008 |
| WO | WO 2009/108816 | 9/2009 |
| WO | WO 2009/141810 | 11/2009 |
| WO | WO 2011/098911 | 8/2011 |
| WO | WO 2013/012528 | 1/2013 |

OTHER PUBLICATIONS

Russian Search Report from related application No. RU 2014148109 dated Jun. 2, 2016, 4 pages.
Extended European Search Report from related application No. EP 18151191.6 dated Apr. 24, 2018, 8 pages.
International Search Report and Written Opinion from related PCT Application No. PCT/IB2014/003282 dated Feb. 5, 2016, 14 pages.
Russian Search Report from related application No. RU 2016129731 dated Jan. 18, 2018, 4 pages.

(56) References Cited

OTHER PUBLICATIONS

Spring. (n.d.) Random House Kememan Webster's College Dictionary. (2010). Retrieved Jun. 25, 2016 from http://www.thefreedictionary.com/spring.
International Search Report and Written Opinion from related PCT Application: PCT/IB2011/000386 dated Jun. 29, 2011, 12 pages.
Extended European Search Report from related EP Application No. 18150461.4 dated Apr. 11, 2018, 9 pages.
Russian Search Report from related application No. RU 2016129732 dated Jun. 8, 2018, 4 pages.
International Search Report and Written Opinion from corresponding PCT Application No. PCT/IB2014/000699 dated Nov. 7, 2014, 13 pages.

\* cited by examiner

CATHETER TIP ASSEMBLED WITH A SPRING

CROSS-REFERENCE TO RELATED APPLICATIONS

This application is a continuation of U.S. patent application Ser. No. 15/703,162, filed on Sep. 13, 2017, which is a continuation of U.S. patent application Ser. No. 14/170,925, filed on Feb. 3, 2014 and issued as U.S. Pat. No. 9,789,283 on Oct. 17, 2017; all of which are incorporated herein by reference in their entirety.

FIELD OF THE INVENTION

The present invention relates to an endovascular catheter, in particular a flexible catheter tip for use, for example, for stent delivery and percutaneous angioplasty. The catheter tip of the invention is specially designed to have features especially useful in percutaneous procedures in which the catheter must traverse stenotic blood vessels, tortuous vessels, or vessels containing previously deployed stents.

BACKGROUND

In standard stent delivery systems, the proximal portion of the catheter is manufactured from materials that make it relatively stiff or inflexible, which endows the catheter with adequate pushability. By contrast, the distal portion of the catheter is manufactured to be rather flexible to allow adequate deliverability of the stent through tortuous vessels to the desired target.

In the case of a balloon catheter, the balloon, which is located at the distal portion of the catheter, is delivered in a deflated state, wrapped around the catheter's inner inflation tube and covered by a crimped stent. The balloon distal shoulder may be fused to the catheter's inner inflation tube. The whole catheter is designed to glide on a guide wire, with the catheter tip serving as the leading part of the catheter to, for example, penetrate a lesion, navigate through a curved vessel, or pass through an already deployed stent within the vessel.

The properties of the catheter tip determine to a large extent whether or not the catheter will catch on the rough surface of the vessel, the surface of vessel lesion or obstruction, or the struts of a previously deployed stent.

Current catheter tips of stent delivery systems and on angioplasty balloon systems are made of plastic material and have a tip shape that is aimed to provide deliverability of the catheter through challenging anatomies. Two parameters may be adjusted to improve deliverability. The catheter tip may be designed to have longitudinal flexibility to accommodate tortuous vessels, and/or the tip shape and its radial rigidity may be modified to avoid collapse of the distal edge of the tip and/or kinking of the proximal neck of the catheter tip when obstacles are encountered. Optimizing both parameters simultaneously in a catheter tip is problematic, as longitudinal flexibility requires a very thin or flexible material, while pushability and radial rigidity require a thick or stiff material.

Therefore, there is a need in the art for an endovascular catheter tip that is longitudinally flexible and pushable and has radial rigidity at its distal end—in particular at the distal edge, to optimize deliverability of the catheter.

SUMMARY OF THE INVENTION

The present invention provides an endovascular catheter tip having longitudinal flexibility, pushability and radial rigidity at its distal end. By longitudinal flexibility is meant an ability to bend along the longitudinal axis (e.g., to facilitate navigation through tortuous vessels). The catheter tip of the invention includes two features. The first feature of the catheter tip includes a spring-like structure, a spring element, that endows the catheter tip with the desired longitudinal flexibility and pushability. The spring element may be made from any suitable material, for example, metal or plastic, and may be manufactured by any of the methods known in the art. In particular, the spring element may have an external diameter that tapers distally, i.e., the diameter decreases from the proximal end to the distal end. Such tapering may decrease the crossing profile of the spring element thereby improving the catheter's deliverability. When tapered, the spring element may further have an inner diameter (lumen diameter) that is constant from the proximal to distal end or tapers at a lesser rate than the outer diameter. The second feature of the catheter tip—the distal end—provides radial rigidity and is rounded and tapered to prevent the distal edge from flaring and catching on, for example, plaque or the strut of a previously implanted stent as the catheter is moved through the vessel. The spring element may act as the second "distal end" feature of the catheter tip. Thus, the spring element provides longitudinal flexibility, radial rigidity, and pushability in the distal-most portion of the catheter tip. By so combining these two features in one catheter tip, the present invention provides a device having otherwise conflicting structural and functional parameters to facilitate deliverability of the catheter.

In one embodiment, the catheter tip further includes a flexible spacer portion, contiguous with the distal end of the balloon and attached to or integrated with the spring element that, in conjunction with the spring element, confers longitudinal flexibility to the catheter tip.

In another embodiment, the spring element may be partially covered by a jacket that connects the balloon shoulder and the spring itself. The jacket may help maintain the natural properties of the spring. In one aspect, the spring element may be embedded in the jacket. Embedding the spring element in the jacket may improve the bond between the spring and the distal fuse section, where the catheter tip connects with the balloon. In a preferred aspect of this embodiment, the jacket covers or embeds a proximal region of the spring element, leaving a distal region, and in particular the distal end, exposed, i.e., uncovered or unembedded. In another aspect of this embodiment the jacket may include a mediating portion similar to the spacer portion that extends proximal of the spring element.

In yet another embodiment, the spring element comprises coils that are tightly packed in a distal section while in a proximal section the spring element includes coils that are spaced apart from each other.

In still another embodiment, the spring element is a wire coil extending to the distal edge of the catheter tip and the distal edge of the coil is smoothed, for example to minimize damage to the vessel wall. In one aspect of this embodiment the distal edge of the coil is smoothed by having a laser polish/weld applied to it. In another aspect of this embodiment, the distal edge of the coil is smoothed by having a bond applied to it.

Thus, the presently claimed catheter tip comprises a differentially tapering spring element, the differentially tapering spring element having an outer diameter that tapers distally at a first rate to a distal edge of a distal end of said catheter tip, and an inner luminal diameter that does not taper at the first rate. The inner luminal diameter may taper at a second rate or may have a constant diameter. The differentially tapering spring element further may be partially covered by a jacket. The jacket may cover a proximal region of the spring element and not a distal region of the spring element, leaving the distal end of the spring element bare, i.e., exposed. The differentially tapering spring element further may be a wire coil having a pitch space between 2 or more coils in a proximal region and/or a middle region of the spring element and tightly packed coils in a more distal region of the spring element.

The presently claimed catheter tip also comprises a combination spring element, the combination including two or more of the following properties: tapering distally, a wire coil having pitch space between 2 or more coils in a proximal region and tightly spaced coils in a distal region, and partially covered by a jacket. In any of these combination spring element embodiments comprising a jacket, the jacket may cover a proximal region of the spring element and not a distal region of the spring element, leaving the distal end of the spring element bare, i.e., exposed. In any of these combination spring element embodiments in which the spring tapers distally, the spring element may have an outer diameter that tapers at a first rate and an inner diameter that does not taper at the first rate. The inner luminal diameter may taper at a second rate or may have a constant diameter.

The apparatus of the invention may be used, for example, for intravascular delivery of prosthetic devices, such as a stent, or for balloon angioplasty. Where a balloon catheter is used, the catheter tip constitutes the portion of the catheter distal to the balloon. In embodiments where the catheter does not have a balloon mounted on it, for example in biliary stent systems where the catheter itself may be expandable, the catheter tip of the invention may be mounted at the end of the expandable catheter to lead the catheter through the biliary duct. Generally, the catheter tip may extend a few millimeters beyond the distal edge of such a catheter.

In addition to the advantage of enhanced deliverability parameters, another desirable effect of the catheter tip of the invention is higher radio-opacity, which may provide the operator with valuable feedback regarding position of the catheter tip during insertion of the catheter into the anatomy to be treated.

DETAILED DESCRIPTION

In order to enhance deliverability of an endovascular catheter by combining two otherwise contradictory parameters into one catheter tip, the apparatus of the invention provides a catheter tip having longitudinal flexibility, pushability and radial rigidity. In particular, the catheter tip of the invention includes a spring element that is not only longitudinally flexible, but also can provide pushability to the catheter tip and may also have radial rigidity, meaning that it can provide radial support to the catheter tip. The catheter tip of the invention includes a distal end. The distal end preferably is made of a material that confers pushability to the tip and has a tapered shape and sufficient radial rigidity to prevent or minimize flaring at the distal edge of the catheter tip, while gliding over a curved guide wire. The distal end of the catheter tip may be the distal portion of the spring element. Alternatively, the distal end of the catheter tip may include a structure that extends beyond the distal end of the spring element.

The spring element may have an external diameter that tapers from the proximal end to the distal end. The lumen of the spring element may have a constant inner diameter or may also taper distally but at a lesser degree than the outer diameter. The spring element may be partially covered or embedded. The covering or embedding material extends over the proximal portion of the spring element, but preferably the distal end or a distal portion of the spring element including the distal end is left exposed. The covering or embedding material may connect the spring element and balloon shoulder or may include a mediating portion, like a spacer, that extends between the spring element and the balloon shoulder.

The spring element may further comprise tightly packed coils to provide pushability to the catheter tip. However, in one embodiment, the spring element includes in a proximal region of the spring two or more coils with pitch spaces between them. As used herein, the term "pitch space" means, in general terms, space between adjacent coils, "pitch" being the width of one complete helix turn as measured along the axis of the spring element.

The novel combined features of the present invention permit an operator to guide an endovascular catheter over a guide wire through tortuous vessels, lesioned or stenotic vessels, or stented vessels with minimal risk of having the distal edge of the catheter tip catch on rough surfaces of the lumen wall or a previously implanted stent and also minimize the risk that the flexible catheter tip will buckle or collapse against the resistance of a vessel stenosis or occlusion.

The apparatus of the invention is discussed and explained below with reference to the accompanying drawings. Note that the drawings are provided as an exemplary understanding of the present invention and to schematically illustrate particular embodiments of the present invention. The skilled artisan will readily recognize other similar examples equally within the scope of the invention. The drawings are not intended to limit the scope of the present invention as defined in the appended claims.

Figure 1:
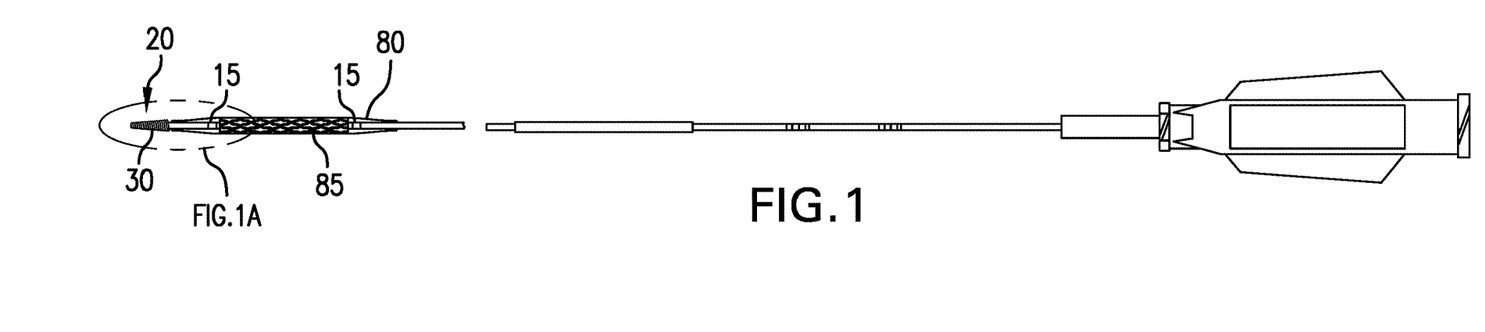
FIG. 1 depicts an embodiment of the catheter tip of the invention that includes a spring element, on a stent delivery system.
Figure 1A:
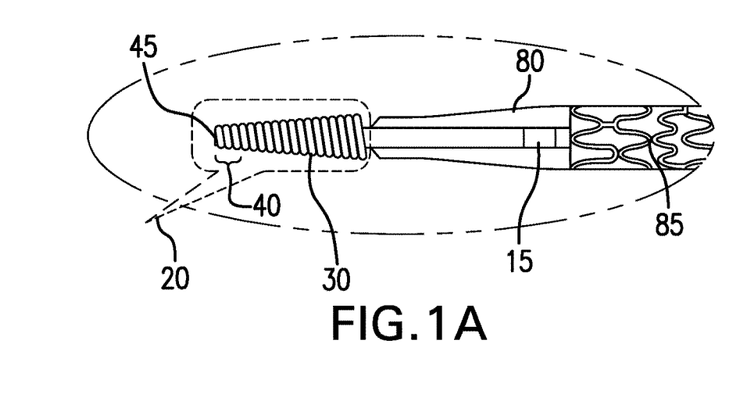
FIG. 1A shows the position of the spring element on the catheter tip.

The catheter tip of the invention includes a spring element, which provides not only longitudinal flexibility, but also pushability to the catheter tip. The spring element may also confer radial rigidity to the catheter tip. An embodiment of the catheter tip 20 of the invention is illustrated in FIGS. 1 and 1A on a balloon-expandable stent delivery system. Depicted in FIG. 1 are a balloon 80, a balloon-expandable stent 85, optional radiopaque markers 15, and the catheter tip 20 including a spring element 30. While illustrated here on a balloon-expandable stent system, the catheter tip 20 may be used on any catheter used to navigate tortuous or partially obstructed lumens. As shown in more detail in FIG. 1A, this embodiment of catheter tip 20 of the invention includes a spring element 30, such as, in this embodiment, an extension spring.

As shown in FIGS. 1 and 1A, where the catheter tip 20 is used on a balloon-expandable stent system, the spring element 30 is located distal of the balloon 80 and in this embodiment tapers distally. The spring element 30 may abut the balloon shoulder, as shown in FIG. 1. Alternatively (not shown), the spring element 30 may be positioned a distance away from the balloon shoulder, in the distal direction, for example 1 or 2 mm, or in the proximal direction, up to the middle of the balloon or the proximal fuse section (i.e., juncture between the proximal end of the balloon and the outer tube of the catheter). The catheter tip 20 of the present invention has a spring element 30 that extends to the distal edge 45 of the catheter tip 20 and provides both pushability and radial rigidity to the distal end portion 40 of the catheter tip 20. In another embodiment, the distal edge 45 of the catheter tip 20 may include a short structure attached to the distal end of the spring element (see FIG. 5B) and made of a polymer, such as a plastic or polyamide. The spring element 30 may have an outer diameter that tapers toward the distal end of the catheter tip.

Where the spring element 30 is positioned at a distance from the shoulder of the balloon 80, the catheter tip 20 may include a spacer portion (not shown) that bridges the distance between the distal end of the balloon 80 and the proximal end of the spring element 30. The spacer portion connects the distal end of the balloon shoulder to the proximal end of the spring element 30 and preferably is longitudinally flexible. Materials used to manufacture the spacer portion may include, for example, a block co-polymer, such as polyether block amide (PEBAX™) polyurethane, or similar appropriate materials. The spacer portion and spring element 30 may be connected by thermal fusing. Alternatively, the spring element 30 may be covered by or embedded in a jacket 38 (as described below for FIG. 2) and the jacket 38 may extend beyond the proximal end of the spring element 30 to the shoulder of the balloon, thereby providing a spacer or mediating portion 39 (see FIG. 6B) between the spring element 30 and balloon 80. Suitable materials for the jacket 38 include polyurethane, a block co-polymer, such as PEBAX™ or other suitable materials. In one aspect, the jacket 38 may be pre-connected to the distal shoulder of the balloon, for example by fusing or gluing. In another aspect, the spring element may be connected to the jacket by thermal heat.

Figure 2:
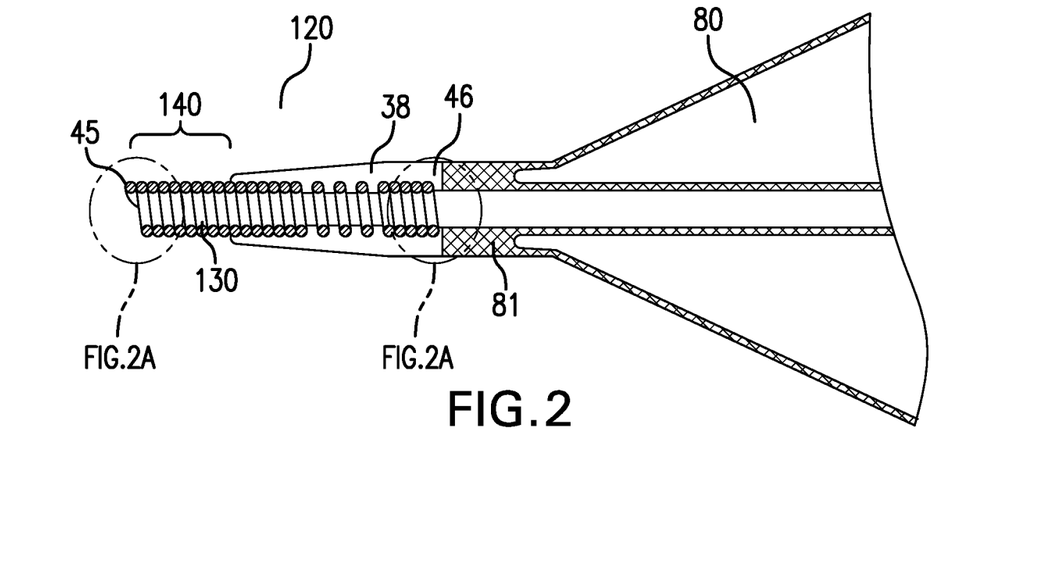
FIG. 2 illustrates a cross-sectional view of an embodiment of the catheter tip of the invention in which the spring element is partially covered and the distal end of the tip is exposed spring.

In another embodiment depicted in FIG. 2, the catheter tip 120, includes a spring element 130 that is fully or partially covered by a jacket 38. The jacket 38 may connect the spring element 30 directly with the distal fuse section 81 or it may include a mediating portion that provides a flexible structure between the balloon shoulder and the spring element. In the aspect of this embodiment in which the jacket 38 includes a mediating portion 39 (see FIG. 6B), the spring element 130 may be positioned a distance away from the balloon shoulder, in the distal direction, for example 1 or 2 mm. In the aspect of this embodiment in which the jacket 38 connects the balloon 80 and the spring element 130 without a mediating portion, as illustrated in FIG. 2, the spring element 130 may abut the balloon shoulder, i.e., at the distal fuse section 81. Alternatively, the spring element may continue proximally past the proximal end of the jacket, for example up to the middle of the balloon 80 or to the proximal fuse section (not shown), i.e., the juncture between the balloon and the outer tube of the catheter body. In either aspect, the jacket 38 may thereby provide an adequate bond between the spring element 130 at the distal fuse section 81 of the balloon 80 to affix the spring element 130 to the balloon 80 and main body of the catheter. The particular jacket 38 embodiment illustrated in FIG. 2 does not include a mediating portion (spacer) and therefore connects the spring element 130 to the balloon shoulder at the distal fuse section 81.

The jacket 38 may help maintain the spring's natural characteristics while at the same time provide a strong embedding material. Because the jacket 38 covers all or part of the spring element, the distal end 140 of the spring element 130 may be left entirely exposed. The length of the exposed portion of the spring element 130 may vary considerably, for example, between about 30 to about 70% of the spring's length, or between about 30% to about 50% of the spring's length, or between about 50% to about 70% of the spring's length, or between about 40% to about 60% of the spring's length, or between about 30% to about 40% of the spring's length. Any spring element, for example spring elements 30, 130, 230, 330 illustrated in FIGS. 1, 2, 3 and 4, may be partially or fully covered or embedded by a jacket 38 in this manner, in accordance with the catheter tip of the invention.

Figure 2A:
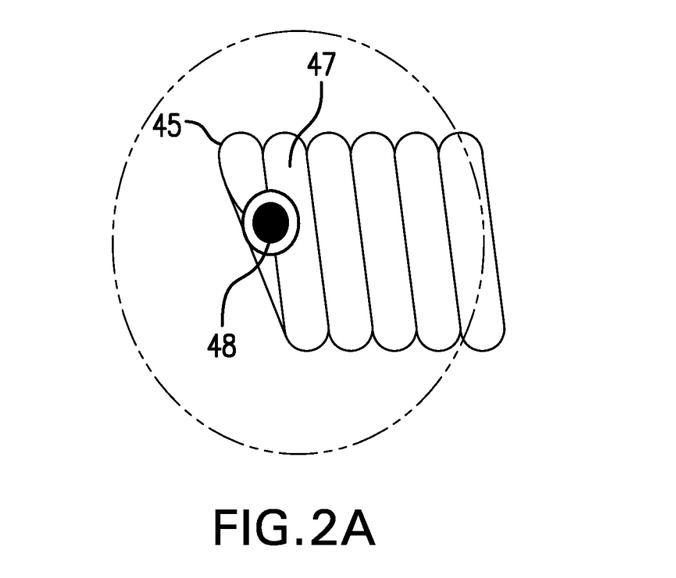
FIG. 2A illustrates one aspect of the distal end of the catheter tip of FIG. 2 in which a bond has been applied to a spring edge.

The spring element 30, 130, 230, 330 may be a wire coil that extends to the distal edge 45 of the catheter tip 20, 120 and is the de facto distal end 40, 140 of the catheter tip. Thus, there may be a need to smooth the end of the wire coil, because the distal edge 45 of the catheter tip may come in direct contact with a vessel wall. It may also be desirable to smooth the proximal end of the wire coil. One solution for smoothing the ends of the wire coil spring element, not illustrated, is to apply a laser polish/weld on the coil end(s), thereby smoothing the ends(s) and at the same time affix the end of the wire coil to the neighboring or adjacent coil 47 of the spring element. The "adjacent coil" 47 may be either the most distal or most proximal coil, depending on whether the distal end or proximal end of the wire coil is being smoothed. An alternative solution is to use an adhesive or any other type of bond 48 to connect the coil wire edge to a neighboring coil 47, as illustrated in FIG. 2A. The bond 48 acts to eliminate the free edge wire coil end, to smooth sharp edges on the end of the wire coil and to affix the end to an adjacent coil. The laser weld or other bond preferably should leave no excess material flow, which—like sharp edges—may cause trauma to the tissue.

In general, the spring element 30, 130, 230, 330 may be tapered distally in order to decrease the crossing profile of the distal edge 45 of the catheter tip. Tapering will result in a decreased entry profile and thereby improve deliverability and crossability through narrowed and/or stenosed vessels and/or calcified lesions. For some applications, it may be preferable that the inner diameter of the tapered spring element (the lumen diameter) does not itself taper. In such embodiments, the spring element has an inner diameter (lumen diameter) that is constant along the entire length of the spring element. In other words, the inner diameter is the same along the spring length, while the outer diameter gradually decreases in the distal direction. Alternatively, the inner diameter of the spring element may narrow distally, but at a lower rate than the narrowing of the outer diameter, i.e., having less taper than the outer diameter. It is the narrowing (rate of decrease) of the outer diameter that determines the actual extent of tapering of the spring element and catheter tip.

One advantage in having a spring with constant or near-constant inner diameter is that it may control and limit internal friction between the spring element and the guide wire that passes therethrough. Another advantage lies in limiting the friction between the spring element and the mandrel on which the catheter is mounted during manufacturing. Exemplary embodiments of tapered spring elements having a constant inner diameter for use in the catheter tips of the invention are illustrated in FIGS. 3 and 4.

One method of tapering the outer diameter of the spring element while maintaining a constant or near constant inner diameter is to manufacture the spring element as a coiled wire from a tapered wire. By "tapered wire" is meant a wire having a decreasing cross-sectional diameter 31 along its length. Such a tapered spring element 230 is illustrated in FIG. 3. In this particular, non-limiting embodiment, the cross-sectional diameter 31 of the wire is 0.1 mm at a first end (proximal end 46 of the wire coil) and the cross-sectional diameter 31 of the wire is 0.05 mm at a second end (distal end 45 of the wire coil). Other gradations of wire cross-sectional diameter 31 may be used, depending on the degree of taper desired for the spring element 230. For example, the cross-sectional diameter of the tapered wire may decrease by about 30-70% between the first end and second end. Obtaining a tapered outer diameter while maintaining a constant inner, luminal diameter for the spring element 230 formed from a tapered wire may be ensured during manufacturing by winding the tapered wire on a fixed diameter mandrel. The inner, luminal diameter of the resultant wire coil spring element 230 remains constant or near constant, and the effect of the decreasing wire diameter will translate into a reduced outer diameter for the resultant spring element 230. Similarly, an inner, luminal diameter having a lesser taper than the outer diameter may be achieved during manufacture by winding the tapered wire on a mandrel having a taper rate less than that of the cross-sectional diameter of the tapered wire.

Figure 4:
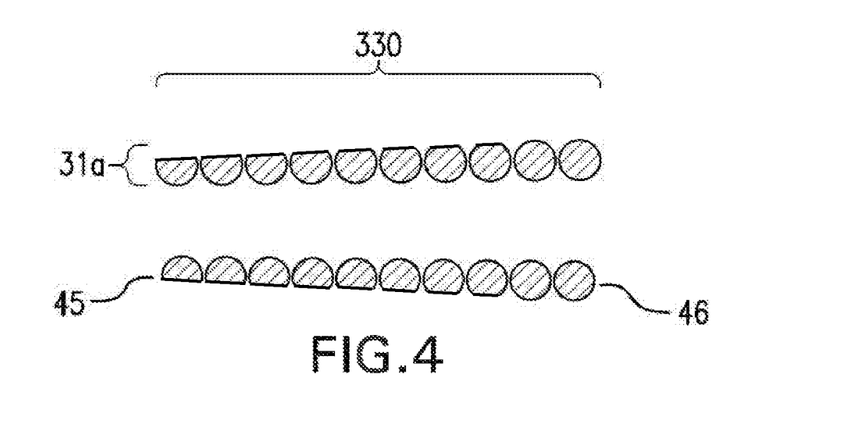
FIG. 4 illustrates a cross-sectional view of an embodiment of a tapered spring tip having a constant internal diameter.

FIG. 4 illustrates another embodiment of a tapered spring element 330 having a distally tapering outer diameter and a constant or near constant inner (lumen) diameter. A method for producing the embodiment of FIG. 4 involves starting with a non-tapered spring element (e.g., a coil having a constant outer diameter along its length), and exposing the outer surface of the spring element to laser radiation or chemical etching, or any other means of grinding or abrading the outer surface of the wire coil, to produce a gradually reduced cross-sectional diameter 31a of the wire coil toward the distal end 45. The coil of the spring element 330 is thereby rendered to taper distally on its outer surface, while the inner luminal diameter remains substantially constant. Thus, in one aspect of this embodiment, the starting wire cross-sectional diameter may be, for example, 100 micrometers and may be reduced in the distal direction by between about 30-70% from the proximal end 46 to the distal end 45 of the spring element 330. After abrading the outer surface of the coils to the desired taper, the spring element 330 may be polished to effect a smooth surface to minimize damage to vessel walls.

Figure 3:
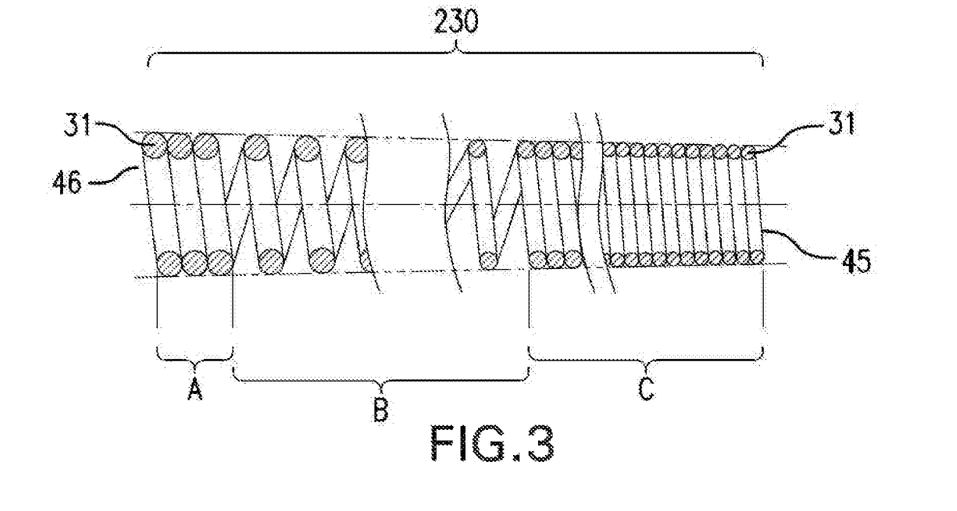
FIG. 3 illustrates a cross-sectional view of an embodiment of a tapered spring element that combines spaced coils and a coil wire with decreasing outer diameter.

The spring elements 130, 230 depicted in FIGS. 2 and 3 further illustrate another feature that may be incorporated into the catheter tip of the invention: spaced coils. In general, the coils in the spring element of the invention are packed tightly with no pitch spaces. The tightly packed coils provide pushability to the catheter tip. However, in one embodiment, a few coils of the spring element 130, 230 have spaces between them. Such spaced coils may be located near the proximal end 46 of the spring element 130, 230 where it is fused to the balloon shoulder or spacer. The number of spaced coils of such a spring element 130, 230 may be in the range of 2-10 coils. Thus, as illustrated in FIG. 3, a first region B of the spring element 230 includes pitch spaces and a second region C has tightly packed coils. Preferably the second region is distal of the first region. The embodiment illustrated in FIG. 2 has a small number of coils with pitch spaces. Exemplary spacing between neighboring spaced coils may be in the range of 0.5-2 times the cross-sectional diameter of the wire.

One objective of including pitch space in a portion of the spring element is to increase the bond strength at the point of connection with the balloon shoulder, the distal fuse section 81. Without being bound by theory, the bond strength may be enhanced because the jacket 38 (FIG. 2) may be pressed into the spaces between the coils. This increases the contact area between the jacket and the spring element, thereby increasing the friction between the spring and jacket, resulting in an increased bond strength in that area.

FIGS. 5A-7B illustrate advantages of the catheter tip of the invention over conventional catheter tips.

Figure 5A:
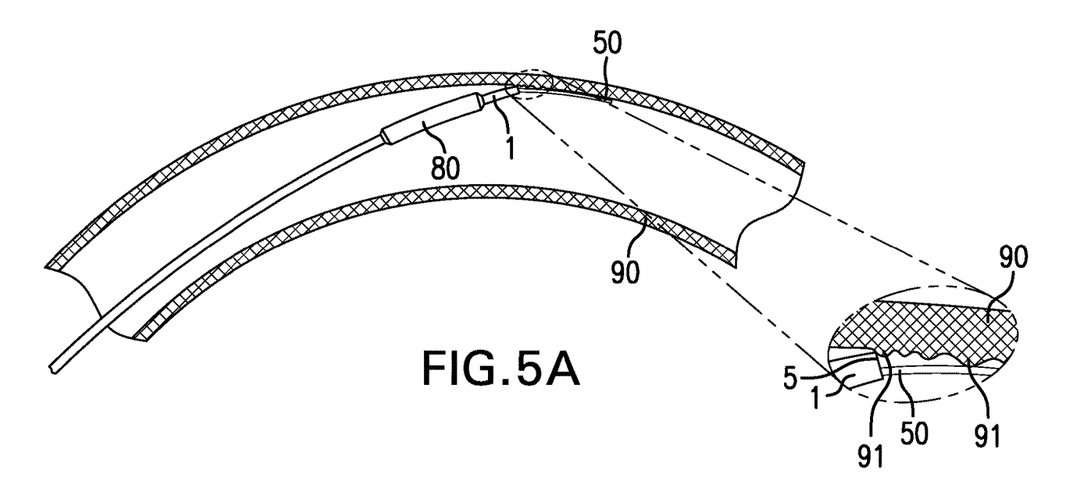
FIG. 5A depicts the conventional catheter tip on a balloon catheter system in a curved vessel.

FIG. 5A depicts how a conventional catheter tip made of a stiff material to achieve good pushability may catch on the rough surface of the lumen of a curved vessel. Depicted in FIG. 5A is a conventional catheter tip 1; a balloon 80 of a balloon-catheter on which the conventional catheter tip 1 is mounted for illustration; and a guide wire 50. As the guide wire 50 contacts a curved portion of a vessel wall 90, it tends to bend longitudinally as shown in FIG. 5A. The conventional catheter tip 1 has less longitudinal flexibility than the guide wire 50. Thus, as shown in more detail in the inset of FIG. 5A, the distal edge 5 of the conventional stiff catheter tip 1 protrudes away from the bent guide wire 50 toward the vessel wall where it can catch on the rough surface 91 of the lumen of the vessel wall 90, making deliverability of the catheter difficult and potentially causing damage to the vessel wall 90. Similarly, where the catheter must traverse a stented vessel, the protruding distal edge 5 of such a conventional device can catch on struts or other structures of the previously deployed stent.

Figure 5B:
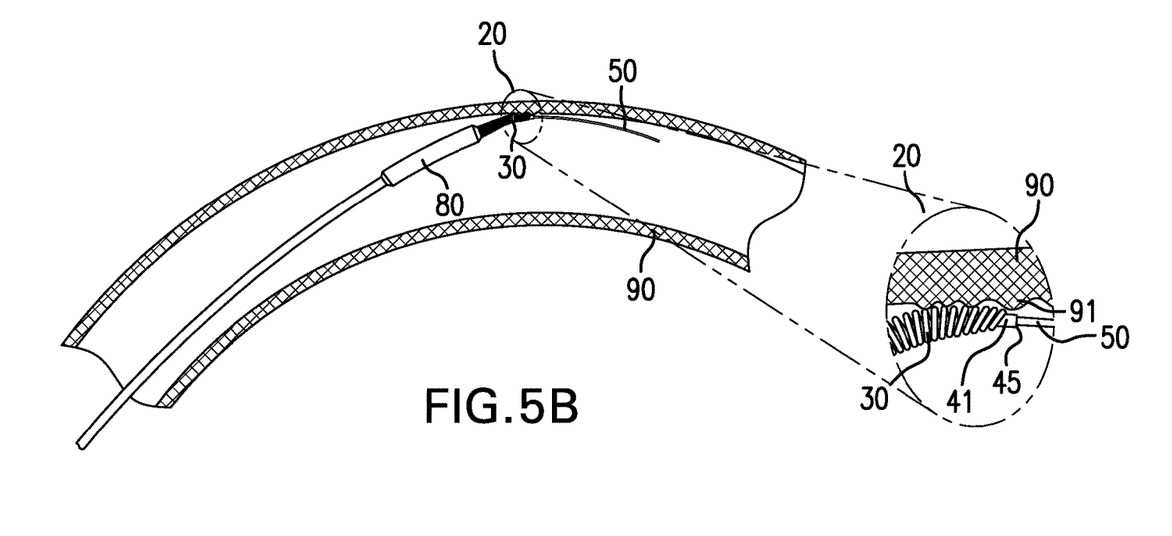
FIG. 5B depicts an embodiment of the flexible catheter tip of the invention on a balloon catheter in a curved vessel.

FIG. 5B, illustrates features of an embodiment of the present invention that minimize the risk that the distal edge of the catheter tip will catch on the rough surface of the lumen wall of a curved vessel. Specifically, FIG. 5B shows a catheter tip 20 including a spring element 30 in a curved vessel, and a balloon 80 of a balloon-catheter on which the catheter tip 20 is mounted for illustration. The spring element 30 is flexible yet has pushability characteristics because of the tight coils, and it is radially rigid. In the catheter tip embodiment depicted in FIG. 5B, the spring element 30 does not extend to the distal edge 45 of the catheter tip 20, but the catheter tip includes a short structure 41 attached to the distal end of the spring element 30, for example by gluing or fusing. The short structure 41 attached to the end coil of the spring element 30 may be made of a polymer, such as a plastic or polyamide. The inset of FIG. 5B shows in greater detail the longitudinal flexibility of the spring element 30. The longitudinal flexibility of the spring element 30 permits the catheter tip 20 to flex easily with the guide wire 50 as it flexes laterally with the curve of the vessel lumen, so that the short structure 41 can track tightly with the guide wire 50 and the distal edge 45 does not protrude and catch on the rough surface 91 of the lumen of the vessel wall 90. In this embodiment, the spring element 30 and the short structure 41 are tapered, as illustrated in the inset of FIG. 5B, which tapering may further reduce the risk that the distal edge 45 will catch on the rough surface 91 of the lumen of the vessel wall 90. The preferred tapered shape of the short structure 41 of the catheter tip 20 may be effected by heating. In embodiments in which the spring element 30 tapers distally and extends to the distal edge 45 of the catheter tip 20, it will similarly operate to track tightly with the guide wire 50 and the distal edge 45 does not protrude and catch on the rough surface 91 of the lumen of the vessel wall 90. In this or any of the other embodiments the spring element 30 may be partially or fully covered with or embedded in a layer of a flexible polymer or similar material, a jacket, to create a smooth surface and improve trackability of the structure without altering the flexible properties of the spring. Examples of materials for such coverings include polyurethane and PEBAX™.

Figure 6A:
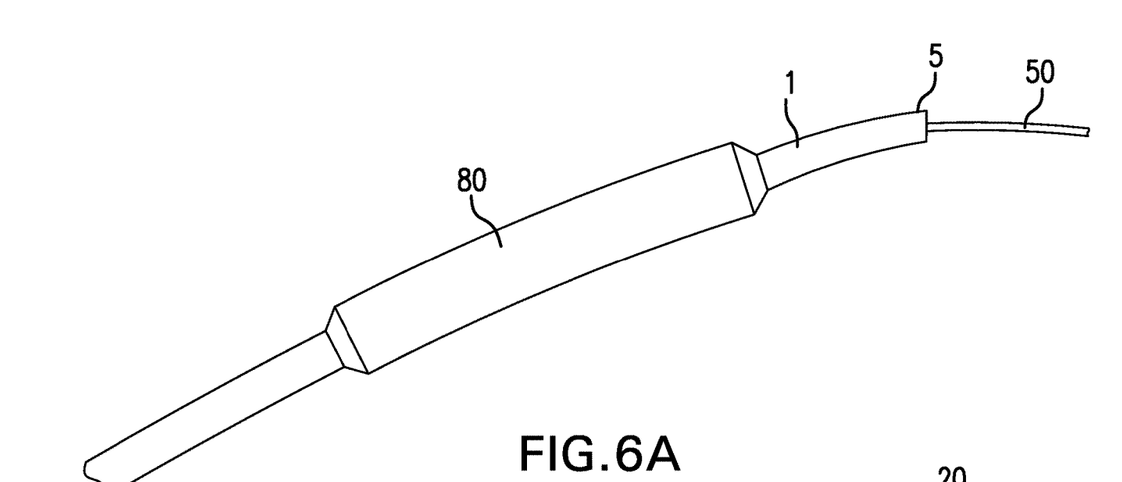
FIG. 6A depicts tip edge protrusion of a conventional catheter tip.

FIG. 6A illustrates a conventional catheter tip 1 mounted on a balloon-angioplasty system, also showing the balloon 80, and the problem in the art of protrusion of the distal edge 5 of the catheter tip 1. The lack of flexibility and the radial rigidity along the length of the conventional catheter tip 1 tends to cause the distal edge 5a of the conventional catheter tip 1 to protrude away from the guide wire 50 as it curves through the vessel. The large inner diameter and thick walls of the distal end of the conventional catheter tip may further contribute to the problem of the protruding distal edge.

Figure 6B:
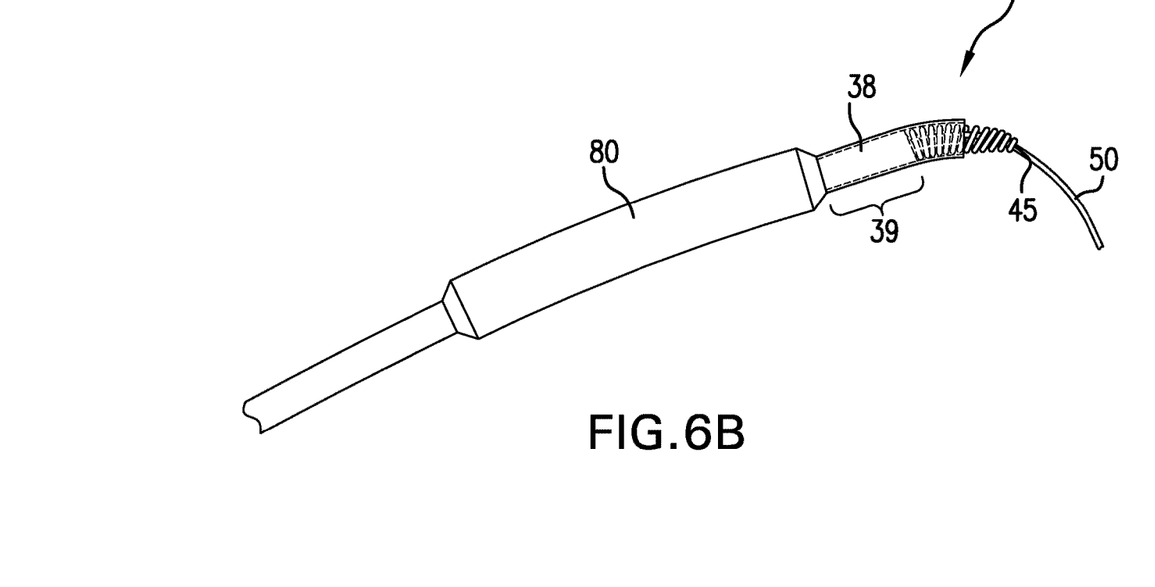
FIG. 6B depicts absence of tip edge protrusion of an embodiment of the flexible catheter tip of the invention having a spring element and a radially rigid distal end.

By contrast, FIG. 6B illustrates how the combination of flexibility and radial rigidity of a catheter tip 20 in accordance with the invention minimizes flaring of the distal edge 45 in an embodiment of the catheter tip of the invention (also mounted on a catheter of a balloon-angioplasty system). Depicted in FIG. 6B is a catheter tip 20 including a jacket 38 and a tapered spring element 30; the balloon 80 of the balloon-angioplasty system; and a guide wire 50. In this particular embodiment, the jacket 38 partially covers the spring element 30 and has a mediating portion 39. The mediating portion 39 of the jacket 38 extends proximal of the spring element 30 to the distal shoulder of the balloon 80. The radial rigidity and the tapered shape of the spring element 30 in combination with the flexibility of the spring element 30 limits protrusion of the distal edge 45 beyond the guide wire. The longitudinal flexibility of the spring element 30 permits the catheter tip 20 to bend with the guide wire, minimizing force on the distal edge 45 from the guide wire, and the radial rigidity of the spring element 30, which extends to the distal edge 45, minimizes plastic deformation. As shown in FIG. 6B, bending of the guide wire 50 does not result in protrusion of the distal edge 45 of such a catheter tip 20 from the guide wire 50. Because the spring element 30 extends to the distal edge 45 of the catheter tip 20 and comprises tightly packed coils, it provides both pushability and radial rigidity to the distal end of the catheter tip 20. Preferably, in this other embodiment the spring element 30 has a distally tapered outer diameter.

Figure 7A:
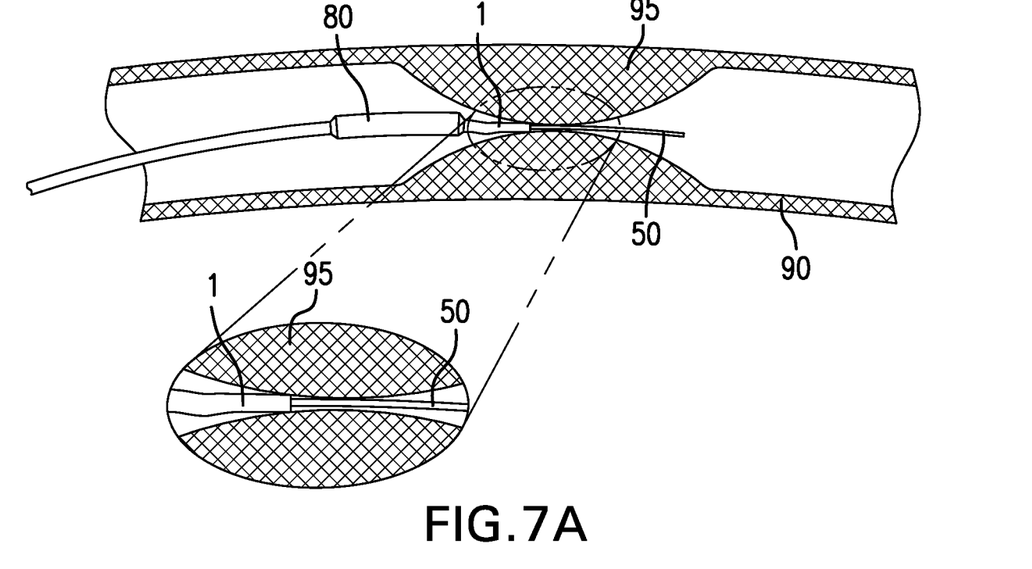
FIG. 7A depicts a conventional catheter tip on a balloon catheter in a stenotic vessel.

The estimated compromise between rigidity and elasticity maintained by a conventional catheter tip may result in kinking when the catheter tip encounters a stenotic portion of a vessel, as illustrated in FIG. 7A. For example, kinking may occur near the distal end of the balloon or any other localized soft or elastic point within the catheter tip. A conventional catheter tip on a balloon catheter is shown in FIG. 7A being pushed through a blood vessel 90 having a stenosis 95. Also depicted is the balloon 80 for the balloon-angioplasty balloon, on which the conventional catheter tip 1 is mounted for illustration, and a guide wire 50. As the conventional catheter tip is advanced through the stenosis 95, the stenotic material causes friction or resistance against the catheter tip, causing the conventional catheter tip 1 to give way to the harder material of the vessel plaque, causing it to kink or buckle, as shown in the insert of FIG. 7A. This is particularly a problem when stenotic material includes significant calcium deposits, which is not uncommon.

Figure 7B:
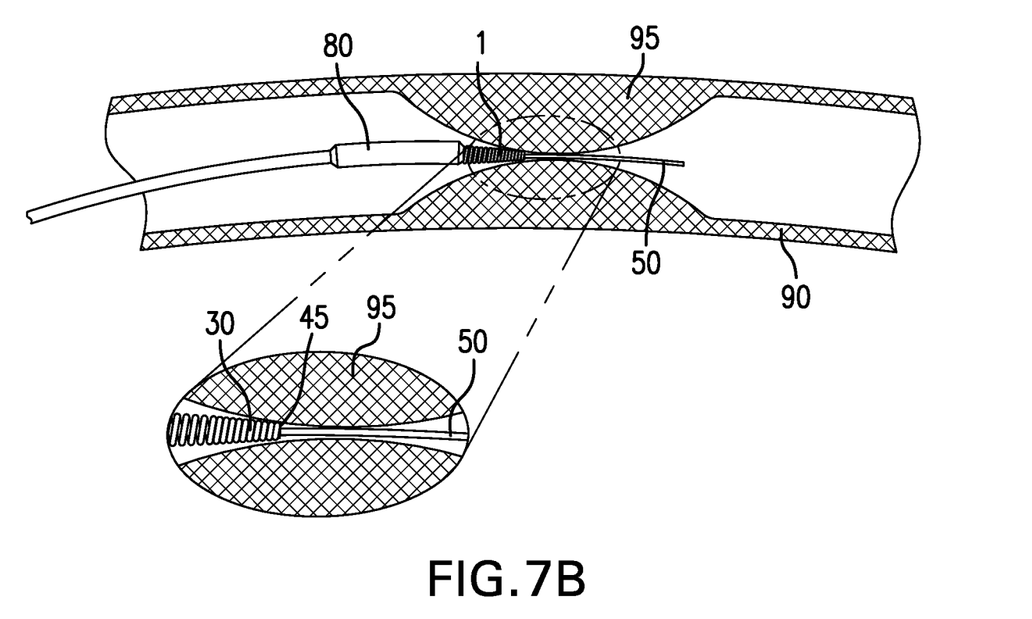
FIG. 7B depicts an embodiment of the flexible, pushable catheter tip of the invention on a balloon catheter system in a stenotic vessel.

By contrast, the flexible catheter tip of the invention provides greater pushability, and it exhibits no kinking because of its flexible body. This is illustrated in FIG. 7B, where an embodiment of the invention mounted on a balloon catheter is shown being pushed through a stenotic vessel. Depicted is a catheter tip including a spring element 30 extending to the distal edge 45; the balloon 80 of a balloon-angioplasty system on which the catheter tip is mounted for illustration; and a guide wire 50. In this particular embodiment, the spring element 30 is a wire coil that includes pitch space between a few coils in a first region, but not in a second region, the second region being distal of the first region. Because the spring element 30 may provide not only longitudinal flexibility and radial support, but also improved pushability to the catheter tip 20, the friction exerted by the stenosis 95 against the catheter tip of the invention will not cause the catheter tip 20 to kink.

Any structure that has the desired properties of longitudinal flexibility, radial rigidity and pushability is suitable as a spring element in accordance with the invention. Examples of a spring element include an extension spring, an accordion plastic tube, and a braided-accordion plastic tube. Some springs, including for example compression springs, are not preferred as spring elements. Extension springs have a predominantly tightly packed coil that is conducive to flexion along the longitudinal axis, without permitting spring compression or deformation, which could negatively impact the pushability of the catheter or control of the catheter tip when the catheter is pushed.

Suitable materials for the spring element include, for example, stainless steel, cobalt chromium, Nitinol or other appropriate materials that would be apparent to one skilled in the art from the description herein. A suitable range for a spring constant for the spring element is 0.3-25 gF/mm. Where the spring element is made of a coiled wire—for example, a stainless steel wire—the diameter of the wire may be in the range of 0.025-0.3 mm, preferably, 0.06-0.2 mm. One skilled in the art would appreciate from these parameters the appropriate wire diameter range for a spring element constructed from other materials. The spring element may be constructed using radiopaque materials to provide the catheter tip with higher radiopacity, thereby allowing improved imaging of the catheter tip.

The embodiments of the catheter tips of the invention are illustrated and described herein mounted on catheters of balloon-expandable stent systems and balloon angioplasty systems. However, it is contemplated the catheter tips may be used on any intravascular catheters, including for example self-expanding stent systems, intravascular catheters used to deliver other intravascular prosthetic devices, or other therapeutic intravascular catheters.

It will be appreciated by persons having ordinary skill in the art that many variations, additions, modifications, and other applications may be made to what has been particularly shown and described herein by way of embodiments, without departing from the spirit or scope of the invention. Therefore it is intended that scope of the invention, as defined by the claims below, includes all foreseeable variations, additions, modifications or applications.

What is claimed is:

1. A flexible catheter, comprising:
   a longitudinal catheter body extending from a proximal end to a distal end; and
   a flexible catheter tip located at said distal end of said catheter body, said flexible catheter tip comprising:
      a spring element having a proximal end and a distal end, said spring element having coils, wherein the proximal length of the spring element includes spaced coils and the spring element does not extend to a distal edge of the flexible catheter tip;
      a distal structure attached to the distal end of the spring element, wherein the distal structure extends beyond the distal end of the spring element and is a polymer material; and
      a jacket partially covering said spring element, wherein a proximal length of said spring element is covered with said jacket, said jacket covering the proximal length but not a distal length of said spring element.

2. A flexible catheter, comprising:
   a longitudinal catheter body extending from a proximal end to a distal end; and
   a flexible catheter tip located at said distal end of said longitudinal catheter body, said flexible catheter tip including a spring element having a proximal end and a distal end, wherein said spring element is a wire coil having spaced coils in a first region and no pitch space between coils in a second region, said second region being distal to said first region, and wherein said spring element tapers distally; and
   a jacket covering said spring element.

3. The flexible catheter of claim 2, wherein the jacket fully covers the spring element.

4. The flexible catheter of claim 2, wherein the jacket fully embeds the spring element.

5. The flexible catheter of claim 2, wherein the jacket partially covers the spring element, said jacket covering a proximal length of the spring element.

6. The flexible catheter of claim 2, wherein the jacket extends to a distal edge of the flexible catheter tip.

7. The flexible catheter of claim 2, wherein the spring element does not extend to a distal edge of the flexible catheter tip.

8. The flexible catheter of claim 7, further comprising a distal structure attached to the distal end of the spring element, wherein the distal structure extends beyond the distal end of the spring element.

9. The flexible catheter of claim 8, wherein the distal structure extends to a distal edge of the flexible catheter tip and is a distal-most end of the flexible catheter tip.

10. The flexible catheter of claim 9, wherein said distal structure is configured to provide radial rigidity to the distal-most end of the flexible catheter tip.

11. The flexible catheter of claim 8, wherein the distal structure is a polymer material.

12. The flexible catheter of claim 1 or 11, wherein the polymer material is selected from the group consisting of plastic and polyamide.

13. The flexible catheter of claim 8, wherein the distal structure is the jacket.

14. The flexible catheter of claim 9, wherein the distal structure tapers distally towards the distal edge of the flexible catheter tip.

15. The flexible catheter of claim 2, wherein the first region comprises 2-10 coils.

16. The flexible catheter of claim 2, wherein the wire coil comprises a cross-sectional diameter, wherein a pitch space between the spaced coils is a distance of about 0.5-2 times the cross-sectional diameter of the wire coil.

17. The flexible catheter of claim 1 or 2, wherein the jacket embeds the spring element.

18. The flexible catheter of claim 1 or 2, wherein the jacket partially embeds the spring element, said jacket embedding a proximal length of the spring element.

19. The flexible catheter of claim 1 or 2, wherein the jacket is a flexible polymer material.

20. The flexible catheter of claim 19, wherein the flexible polymer material is selected from the group consisting of: polyurethane, a block co-polymer, and PEBAX™.

21. The flexible catheter of claim 1 or 2, wherein said spring element is an extension spring.

22. The flexible catheter of claim 1 or 2, wherein the spring element has an outer diameter that tapers distally at a first rate, and an inner luminal diameter that tapers distally at a second rate, said second rate being different from said first rate.

23. The flexible catheter of claim 22, wherein the inner luminal diameter is substantially constant.

24. The flexible catheter of claim 22, wherein said second rate is lower than said first rate.

25. The flexible catheter of claim 22, wherein said spring element is a wire coil, and wherein the wire coil has a decreasing cross-sectional diameter from the proximal end of the spring element to the distal end of the spring element.

26. The flexible catheter of claim 25, wherein the wire coil comprises a first cross-sectional diameter of 0.1 mm at the proximal end of the spring element, and a second cross-sectional diameter of 0.05 mm at the distal end of the spring element.

27. The flexible catheter of claim 25, wherein the decreasing cross-sectional diameter of the wire coil decreases by 30-70% between the proximal end of the spring element and the distal end of the spring element.

28. The flexible catheter of claim 1 or 2, wherein said jacket comprises a mediating portion located proximal of the proximal end of said spring element.

29. The flexible catheter of claim 28, wherein said flexible catheter is a balloon catheter comprising an inflatable balloon, wherein the mediating portion is a flexible spacer portion contiguous with a distal end of the inflatable balloon and attached to the proximal end of the spring element, said mediating portion positioning the spring element a distance away from the distal end of the inflatable balloon.

30. The flexible catheter of claim 1 or 2, wherein said flexible catheter is a balloon catheter comprising an inflatable balloon, and wherein the jacket connects a distal end of the inflatable balloon to the spring element.

31. The flexible catheter of claim 30, wherein the spring element abuts the distal end of the inflatable balloon.

32. The flexible catheter of claim 1 or 2, wherein said jacket extends proximally beyond the proximal end of said spring element.

33. The flexible catheter of claim 1 or 2, wherein said flexible catheter is a balloon catheter comprising an inflatable balloon, said jacket is directly connected to said inflatable balloon, wherein said jacket extends over at least a portion of said inflatable balloon.

34. The flexible catheter of claim 1 or 2, wherein said jacket extends about a circumference of said spring element.

35. The flexible catheter of claim 1 or 2, wherein a material of the spring element is selected from the group consisting of: stainless steel, cobalt chromium, and Nitinol™, and wherein a spring constant for the spring element is in a range of 0.3 to 25 gF/mm.

36. The flexible catheter of claim 1 or 2, wherein said spring element is a wire coil, and wherein a diameter of the wire coil is in a range of one of 0.025 to 0.3 mm and 0.06 to 0.2 mm.

37. The flexible catheter of claim 1 or 2, wherein the spring element extends to a distal edge of the flexible catheter tip.

38. The flexible catheter of claim 1 or 2, wherein an outer surface of the spring element has a decreasing cross-sectional diameter from a proximal end of the spring element to a distal end of the spring element.

* * * * *